United States Patent [19]
Clark

[11] Patent Number: 5,435,146
[45] Date of Patent: Jul. 25, 1995

[54] METHOD AND APPARATUS FOR DETERMINING RELATIVE HUMIDITY

[75] Inventor: Daniel R. Clark, Fayetteville, N.Y.

[73] Assignee: Carrier Corporation, Syracuse, N.Y.

[21] Appl. No.: 311,229

[22] Filed: Sep. 23, 1994

[51] Int. Cl.$^6$ .............................................. G05D 22/00
[52] U.S. Cl. ........................................ 62/126; 62/130; 62/176.1; 73/29.02; 374/28
[58] Field of Search ................. 62/125, 126, 127, 129, 62/130, 228.4, 228.5, 176.1, 176.3, 176.6; 73/29.01, 29.02, 335.01; 340/602; 374/17, 18, 19, 20, 28, 16; 236/44 R, 44 A, 44 C; 165/20, 21

[56] References Cited

U.S. PATENT DOCUMENTS

| | | | |
|---|---|---|---|
| 3,265,301 | 8/1966 | Amdur et al. | 73/29.01 X |
| 3,926,052 | 12/1975 | Bechtel | 374/20 X |
| 4,386,502 | 6/1983 | Umezu et al. | 62/129 |
| 4,526,011 | 7/1985 | Logan et al. | 62/176.1 X |
| 4,554,793 | 11/1985 | Harding, Jr. | 374/20 X |

Primary Examiner—Harry B. Tanner

[57] ABSTRACT

A method for determining the relative humidity of the air entering the cooling heat exchanger of an air conditioning system as well as an apparatus for implementing the method. The cooling capacity of the system is varied and, if occurring, the transition between a condition where moisture is condensing in the heat exchanger and a condition where moisture is not condensing in the heat exchanger. At this transition, the temperatures of the exiting air and the entering air are measured. From the measured exiting air temperature, state point of the saturated exiting air can be determined. From the exiting air state point and the entering air state point, the entering air relative humidity can be determined. If no condensation occurs even at maximum cooling capacity, the maximum that the relative humidity of the entering air can be determined. If condensation continues even at minimum cooling capacity, the minimum that the relative humidity of the entering air can be determined.

8 Claims, 4 Drawing Sheets

METHOD AND APPARATUS FOR DETERMINING RELATIVE HUMIDITY

BACKGROUND OF THE INVENTION

This invention relates generally to air cooling or air conditioning systems. More specifically, the invention relates to a method and apparatus for determining the relative humidity of air entering the cooling heat exchanger of an air conditioning system.

It is well known that environmental comfort level is not just a function of temperature. Other factors, such as carbon dioxide level and the presence of smoke, dust, pollen and other pollutants can also be detrimental to air quality. One important contributor to comfort level is relative humidity. For optimum comfort, the relative humidity of the surrounding air must be maintained within a certain range. Control of relative humidity is important not only because of its effect on human comfort but also because either excessively moist or excessively dry conditions can be detrimental to equipment, furniture, buildings and the like.

Advances in the air conditioning art have led to the ability to more precisely and independently control not only air temperature in a conditioned space but also other variables such as relative humidity. One such advance is an air conditioning system having a variable cooling capacity. This capability is achieved in newer, more sophisticated vapor compression systems by providing variable speed motors to drive the compressor and heat exchanger fans. Proper control of such systems to achieve desired relative humidity levels requires that the relative humidity in the conditioned space be known. A control device can then use that information together with other parameters, such as temperature, of the air in the space to determine the proper operating mode for the system.

Most hygrometric devices have one or more of the attributes of being expensive, bulky and unreliable, all of which are undesirable in an air conditioning system. What is needed is a simple and inexpensive way to determine the relative humidity of the air in the conditioned space so that the controller of the system can take the proper action to bring and maintain the relative humidity within a desired range.

SUMMARY OF THE INVENTION

The present invention is a method, as well as an apparatus for implementing the method, for determining the relative humidity in the air entering the air cooling heat exchanger of an air conditioning system. Since the air entering the heat exchanger is being drawn from the space to be conditioned, and absent some other heating, cooling or dehumidification process occurring between the system air intake and the cooling heat exchanger, the relative humidity of the entering air is the same as the air in the space to be conditioned. Thus, measuring relative humidity at the heat exchanger is equivalent to measuring relative humidity in the space.

The invention does not directly measure relative humidity but rather measures and detects other parameters of the system and of the air flowing through it and calculates, from these parameters, the relative humidity of the entering air. The invention is not capable of calculating relative humidity over the entire range of possible relative humidity values for a given condition. That is, there can be extremely high or extremely low values of relative humidity that the method of the invention is unable to determine and that the apparatus cannot calculate. The method and apparatus of the invention can, however, determine that the relative humidity is "out of range high" or "out of range low." This ability should, in general, be sufficient to serve as an input to a controller for an air conditioning system.

In the method and apparatus of the invention, the temperatures of the air entering and leaving the air cooling heat exchanger of a variable cooling capacity air conditioning system are measured while varying the cooling capacity. At some capacity, there may be a transition between a condition where moisture in the entering air is condensing in the heat exchanger to a condition where moisture is not condensing. At this transition point, the exiting and entering air temperatures are measured. From the exiting air temperature and the knowledge that the exiting air is at or near saturation, the state point of the exiting air can be determined by use, for example, of a psychrometric chart. From the knowledge that the moisture content of the air exiting are the same and from the entering air temperature, the relative humidity of the air entering the heat exchanger can be determined by use, for example, of the same psychrometric chart. As discussed above, the relative humidity of the entering air is the same as the air in the intake to the air conditioning system. Thus the relative humidity in the space to be conditioned has been determined. This information can be supplied to the controller of the air conditioning system as an input to a control system that determines the operating mode of the system.

The condition of the air entering the system may be such that, even at minimum cooling capacity, moisture continues to condense in the air cooling heat exchanger. In this condition, no transition will be detected and therefore the actual relative humidity cannot be determined. It will, however, be possible to say that the relative humidity of the entering air can be no lower than some value. Similarly, the condition of the entering air may be such that, even at maximum cooling capacity, no moisture condenses in the air cooling heat exchanger. In this condition, no transition will be detected and therefore the actual relative humidity cannot be determined. It will, however, be possible to say that the relative humidity of the entering air can be no higher than some value.

The temperature sensing devices necessary to practice the invention are relatively inexpensive and are already installed in many air conditioning systems. The practice of the invention requires a condensation sensor. Such a sensor need be nothing more than a simple moisture detector such as an electrode pair. The algorithms necessary to calculate the state point of the exiting air at saturation and the relative humidity of the entering air can easily be programmed into a readily available and relatively inexpensive microprocessor as part of the overall controller of the system.

BRIEF DESCRIPTION OF THE DRAWINGS

The accompanying drawings form a part of the specification. Throughout the drawings, like reference numbers identify like elements.

DESCRIPTION OF THE PREFERRED EMBODIMENT

Figure 1:
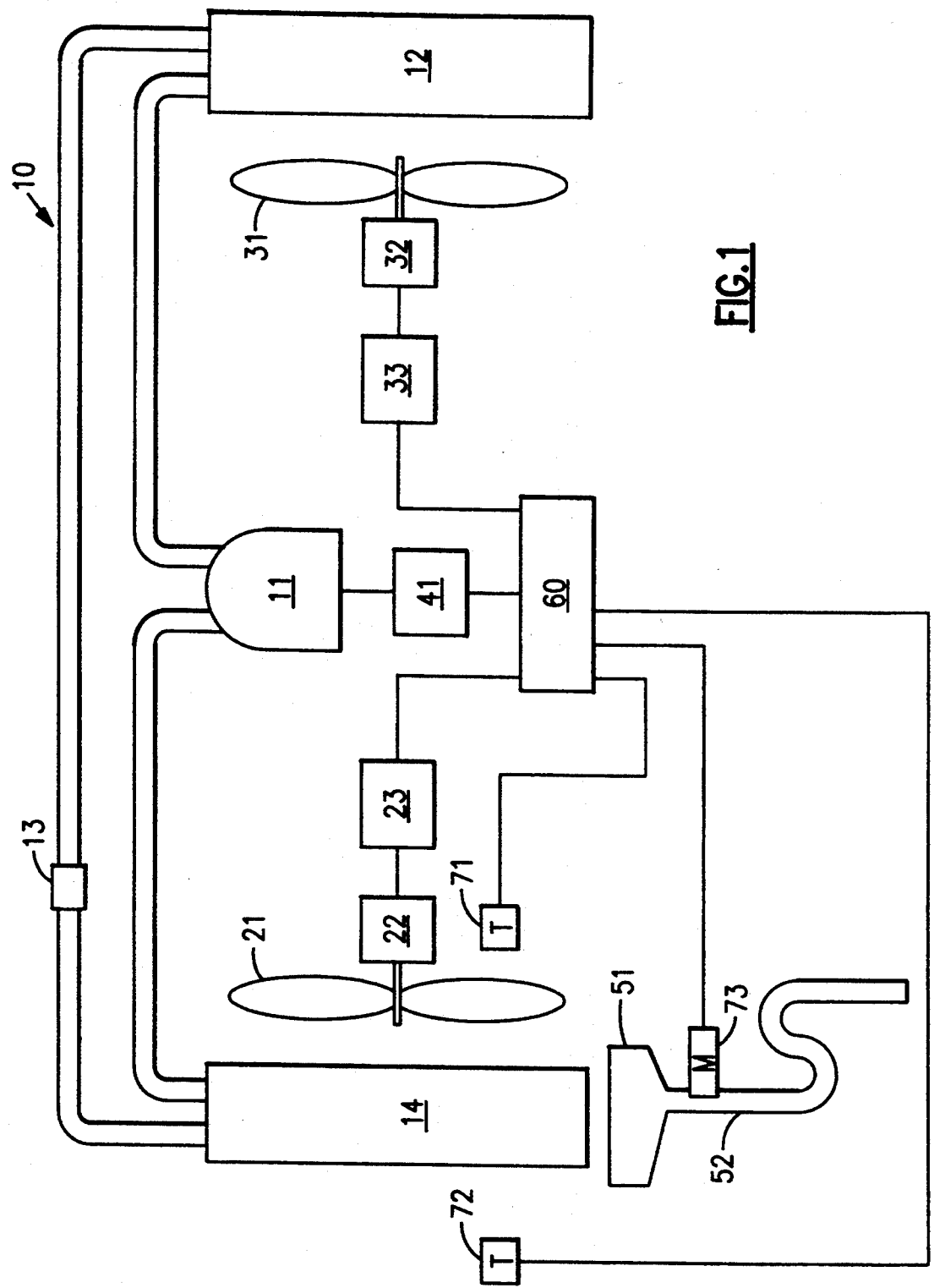
FIG. 1 is a schematic diagram of an air conditioning system employing the apparatus of the present invention.

FIG. 1 depicts an air conditioning system having the components and interconnections of the apparatus of the present invention. The primary components of air conditioning system 10 are compressor 11, outside heat exchanger 12, expansion device 13, and inside heat exchanger 14. Inside fan 21, driven by inside fan motor 22, causes air from the space the system serves to flow through inside heat exchanger 14. Outside fan 31, driven by outside fan motor 32 causes external, usually outside, air to flow through outside heat exchanger 12. System 10 has a variable capacity. This is possible because at least the motor of compressor 11, and preferably inside fan motor 22 and outside fan motor 32, can be varied in speed under the control of, respectively compressor motor controller 41, inside fan motor controller 23 and outside fan motor controller 33. Collector 51 collects condensate draining from inside heat exchanger 14. Condensate drain 52 is a conduit that conducts condensate to a suitable location.

Temperature sensor 71 senses the temperature of the air entering inside heat exchanger 14. Temperature sensor 72 senses the temperature of the air exiting inside heat exchanger 14. Condensate sensor 73, placed in a suitable location such as condensate drain 52, detects condensate draining from inside heat exchanger 14. All three of these sensors provide signals to computer 60. Computer 60 uses these inputs, as well as others, to control the operating mode and capacity of system 10.

System 10 is a vapor compression system that is capable of cooling only and therefore inside heat exchanger 14 functions as an evaporator at all times during system operation. The method and apparatus of the present invention are equally adaptable for use in a reversible vapor compression refrigeration system (popularly known as a heat pump). If desired, and if atmospheric conditions permit, the method and apparatus of the present invention could be used with whichever heat exchanger (outside or inside) is operating as an evaporator at a given time. The method and apparatus, however, are most suitably used with only the inside heat exchanger even in a reversible system. The method and apparatus are adaptable to use with any variable capacity air conditioning system.

Figure 2:
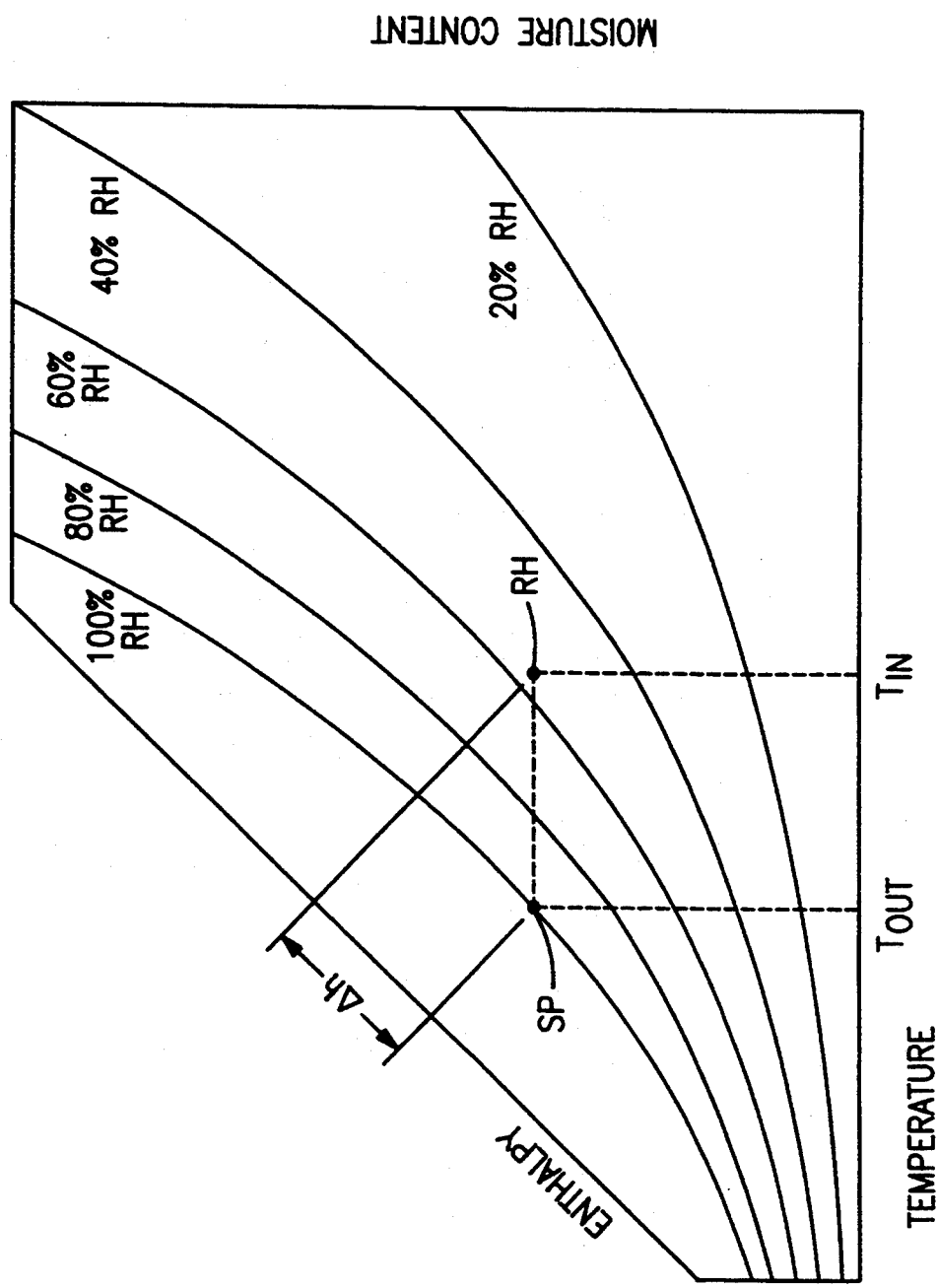
FIG. 2 is a psychrometric chart illustrating an application of the present invention in one situation.

FIG. 2 depicts a portion of a psychrometric chart and is useful to illustrate the principle upon which the invention is based. Referring also to FIG. 1, when, according to the control program in computer 60, there is a need to measure relative humidity in the entering air, computer 60 issues signals to compressor motor controller 41 to vary the speed of compressor 11, thus varying the cooling capacity of system 10. As the cooling capacity is varied, there will probably be a capacity at which there is a transition from a condition where condensate is forming in heat exchanger 14 to a condition where no condensate is forming. Sensor 73 will detect this transition by sensing the onset or cessation of condensate drainage. At the point where the transition occurs, the air exiting heat exchanger 14 is saturated, or has a relative humidity of 100 percent. At the transition point, sensors 72 and 71 measure the temperatures of, respectively, the air exiting and the air entering heat exchanger 14. Because the exiting air is at saturation, it is possible to locate state point SP by entering the psychrometric chart with the exiting air temperature $T_{out}$. The air entering heat exchanger 14 is at the same humidity ratio as the air exiting, Therefore, by knowing the state point of the exiting air and the entering air temperature $T_{in}$, it is possible to determine, from the pyschrometric chart, the relative humidity of the entering air.

Figure 3:
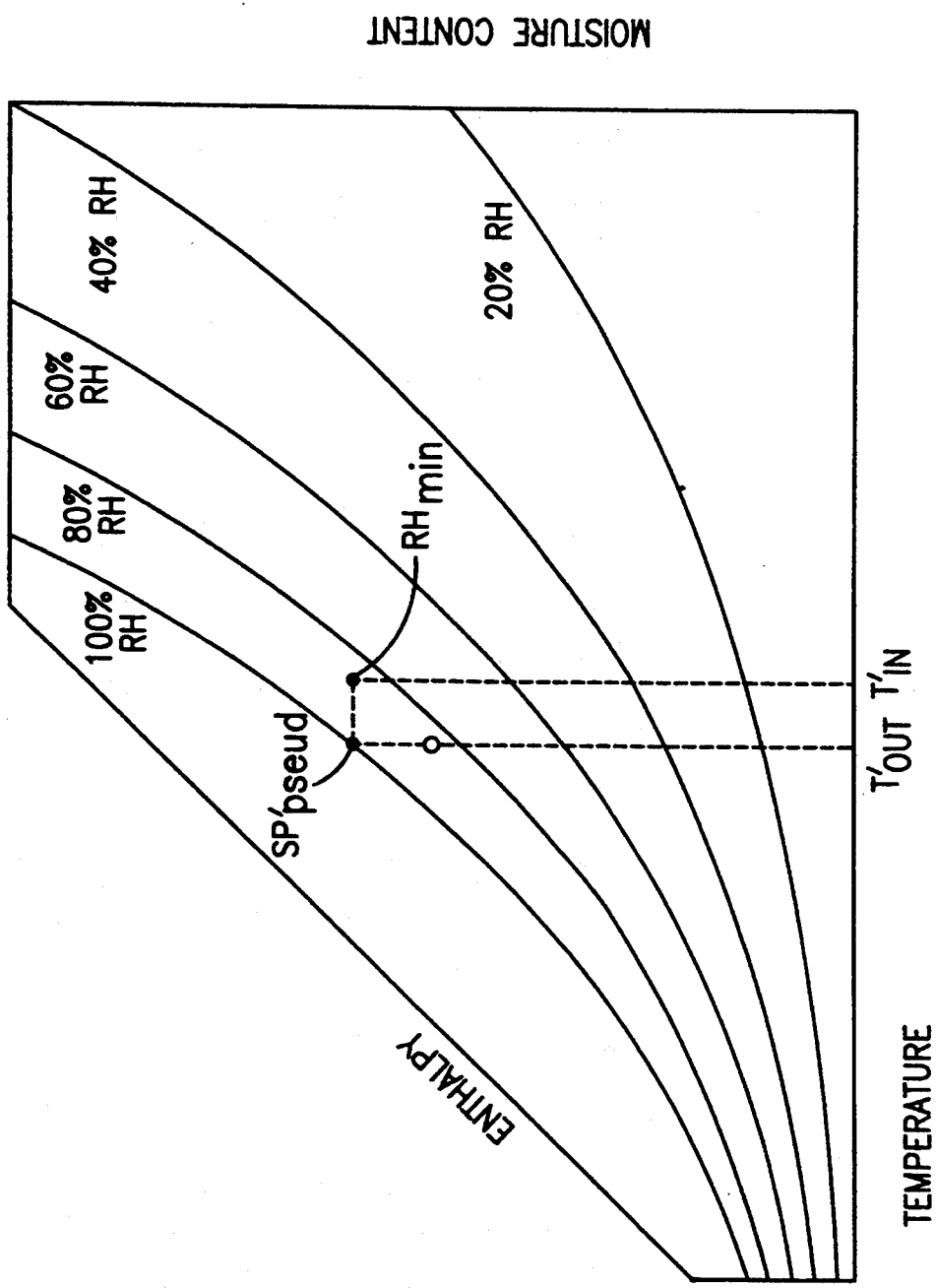
FIG. 3 is a psychrometric chart illustrating an application of the present invention in a second situation.

It is possible that, if the entering air has a high enough relative humidity, there will still be condensate produced even with system 10 operating at minimum capacity, that is, condensate will be produced over the entire range of system cooling capacity and there will be no transition observed. In this case, the temperature of the exiting air is measured while operating at minimum capacity and a "pseudo" state point is determined. Then, using this pseudo state point and the entering air temperature to determine a minimum relative humidity of the entering air, that is, the actual relative humidity of the entering air has not been determined but only that it cannot be less than if the pseudo state point of the exiting air were an actual state point at saturation. FIG. 3 illustrates this, with $SP'_{pseud.}$ being the point of saturation for air having a temperature of $T'_{out}$ and $RH_{min}$ being the relative humidity of air having temperature $T'_{in}$ and the same humidity ratio as saturated air at temperature $T'_{out}$.

Figure 4:
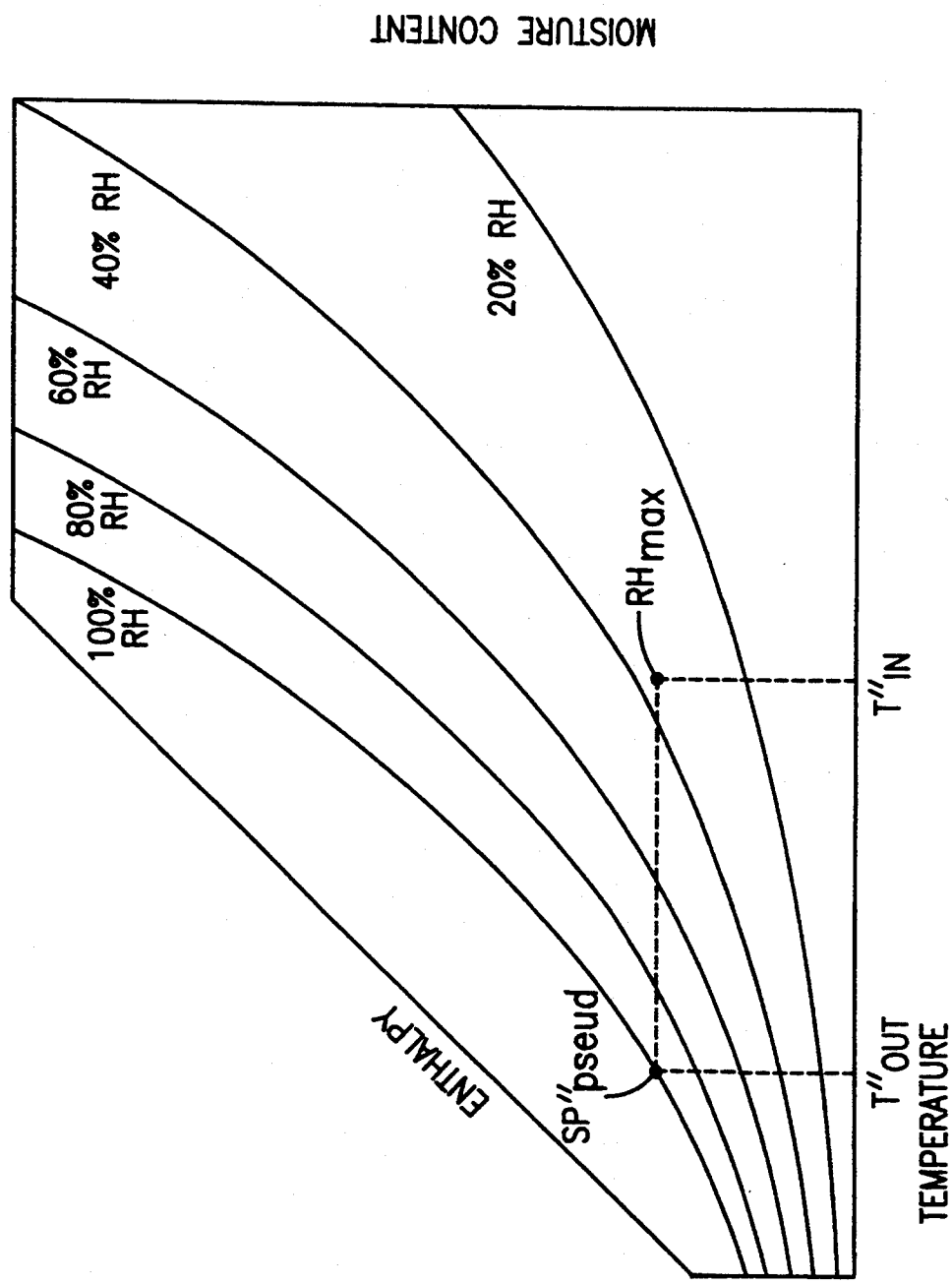
FIG. 4 is a psychrometric chart illustrating an application of the present invention in a third situation.

Similarly, it is possible that, if the entering air has a low enough relative humidity, there will be no condensate produced even with system 10 operating at maximum capacity, that is, there is no transition observed. In this case, the temperature of the exiting air is measured while operating at maximum capacity and a "pseudo" state point is determined. Then, using this pseudo state point and the entering air temperature to determine a maximum relative humidity of the entering air, that is, the actual relative humidity of the entering air has not been determined but only that it cannot be more than if the pseudo state point of the exiting air were an actual state point at saturation. FIG. 4 illustrates this, with $SP''_{pseud.}$ being the point of saturation for air having a temperature of $T''_{out}$ and $RH_{max}$ being the relative humidity of air having temperature $T''_{in}$ and the same humidity ratio as saturated air at temperature $T''_{out}$.

Although a graphical pyschrometric chart was used above to illustrate the operation of the invention, the same information can be provided in the form of equations or tables. Such equations or tables can be programmed into a suitable subroutine of the control program in computer 60 to accomplish the calculations necessary to determine state points and relative humidity.

In practicing the method of the invention, it might be best to start the relative humidity determination at minimum system cooling capacity and gradually increase cooling capacity until detector 73 first detects condensate. Thus, there would be no concern of the time necessary for the detector to dry off after the transition from condensation to no condensation. On the other hand, the test would be less noticeable to occupants of the space served by the system if the test started with operation at maximum cooling capacity and decrease capacity until detection of the transition from condensation to no condensation.

Under normal conditions, some condensation occurs before the bulk air temperature of the air exiting the cooling heat exchanger reaches saturation temperature. More accurate results may therefore be obtained by using a high, for example 95 percent, relative humidity to determine the exiting air state point or pseudo state point rather than 100 percent relative humidity.

The method and apparatus of the invention can also be used to monitor the performance of the associated cooling system. Referring again to FIG. 2, the enthalpy of the entering and the enthalpy of the exiting air can be determined from the respective state points. The difference in these two values can be compared to the expected enthalpy difference. Computer 60 could be programmed with a suitable subroutine to provide a signal if there is a significant difference between actual and expected enthalpy change.

I claim:

1. A method of determining the relative humidity of air entering an air cooling heat exchanger of a variable capacity air cooling system comprising the steps of:
   operating said system at various cooling capacities until, at a particular cooling capacity, one of the following conditions exists:
      Condition A—at some system cooling capacity between maximum and minimum, there is a transition between operation with moisture condensing on said heat exchanger and operation with moisture not condensing on said heat exchanger,
      Condition B—at minimum cooling capacity, moisture continues to condense on said heat exchanger, or
      Condition C—at maximum cooling capacity, moisture still does not condense on said heat exchanger;
   determining, when operating at said particular cooling capacity, the temperature of the air entering said heat exchanger and the change in value of a physical property of the air due to its passage through said heat exchanger;
   determining from said entering air temperature and said changed value of a physical property of the air, the state point of the air exiting said heat exchanger;
   determining, from said state point and said entering air temperature,
      if Condition A exists, the relative humidity of the air entering said cooling heat exchanger,
      if Condition B exists, the minimum relative humidity that the air entering said cooling heat exchanger can be and,
      if Condition C exists, the maximum relative humidity that the air entering said cooling heat exchanger can be.

2. The method of claim 1 in which said physical property of air is its temperature.

3. The method of claim 1 in which said physical property of air is its enthalpy.

4. The method of claim 1 in which:
   where Condition A exists, said state point is a saturation state point and
   where Condition B or C exists, said state point is a psuedo saturation state point.

5. Apparatus for determining the relative humidity of air entering an air cooling heat exchanger of a variable capacity air cooling system (10) comprising:
   means (60, 41) for operating said system at various cooling capacities until, at a particular cooling capacity, one of the following conditions exists:
      Condition A—at some system cooling capacity between maximum and minimum, there is a transition between operation with moisture condensing on said heat exchanger and operation with moisture not condensing on said heat exchanger,
      Condition B—at minimum cooling capacity, moisture continues to condense on said heat exchanger, or
      Condition C—at maximum cooling capacity, moisture still does not condense on said heat exchanger;
   means (73) for sensing the presence of condensate in said heat exchanger;
   means (71, 72,60) for determining, when operating at said particular cooling capacity, the temperature of the air entering said heat exchanger and the change in value of a physical property of the air due to its passage through said heat exchanger;
   means (60) for determining from said entering air temperature and said changed value of a physical property of the air, the state point of the air exiting said heat exchanger;
   means (60) for determining, from said state point and said entering air temperature,
      if Condition A exists, the relative humidity of the air entering said cooling heat exchanger,
      if Condition B exists, the minimum relative humidity that the air entering said cooling heat exchanger can be and,
      if Condition C exists, the maximum relative humidity that the air entering said cooling heat exchanger can be.

6. The apparatus of claim 5 in which
   said operating means comprise a control computer and a variable speed motor controller;
   said means for determining the temperature of air entering said heat exchanger is a temperature sensor; and
   said means for determining the change in value of a physical property of air comprises means for computing the change in enthalpy of air passing through said heat exchanger.

7. The apparatus of claim 5 in which
   said operating means comprise a control computer and a variable speed motor controller;
   said means for determining the temperature of air entering said heat exchanger and said means for determining the change in value of a physical property of air comprise a temperature sensor placed so as to be able to sense the temperature entering said heat exchanger,
   a temperature sensor placed so as to be able to sense the temperature exiting said heat exchanger and
   means for computing the difference in temperature between air entering said heat exhanger and air exiting said heat exchanger.

8. The apparatus of claim 5 in which said condensate sensing means comprises a moisture detector.

* * * * *